(12) United States Patent
Blake

(10) Patent No.: US 6,715,492 B1
(45) Date of Patent: Apr. 6, 2004

(54) MANUFACTURING METHOD FOR ANATOMICALLY ACCURATE ABBREVIATED CONDOMS

(76) Inventor: Rory P. Blake, 3216 Chaucer Dr., Charlotte, NC (US) 28210

( * ) Notice: Subject to any disclaimer, the term of this patent is extended or adjusted under 35 U.S.C. 154(b) by 51 days.

(21) Appl. No.: 10/156,154

(22) Filed: May 28, 2002

Related U.S. Application Data

(60) Provisional application No. 60/293,223, filed on May 25, 2001.

(51) Int. Cl.[7] ................................................. A61F 6/02
(52) U.S. Cl. .......................... 128/842; 128/844; 128/918
(58) Field of Search .............................. 128/842, 844, 128/918; 624/347–353

(56) References Cited

U.S. PATENT DOCUMENTS 5,598,850 A * 2/1997 Miller ......................... 128/842
6,035,854 A * 3/2000 Blake ......................... 128/844
6,145,507 A * 11/2000 Hardy ......................... 128/918
6,298,853 B1 * 10/2001 Blake ......................... 128/844

* cited by examiner

Primary Examiner—Michael A. Brown
(74) Attorney, Agent, or Firm—Peter Gibson

(57) ABSTRACT

A positive mold form possessing a head portion including a reservoir portion, two bilaterally symmetric lobe portions, and a ridge line separating the head portion from a shaft portion has a perforated circumference connected to a bore in the shaft to which negative pressure is applied for holding a backing strip in position. Adhesive is applied to the exterior surface of the backing strip while negative pressure is maintained upon the same. Curing of the adhesive with a UV radiation source is suggested as if use of water soluble adhesive which is effective when immersed in isotonic fluid. An upper part of the positive mold form is coated with liquid elastomer and the resulting layer of elastomer cured with temperature reduction. Positive pressure applied to the perforated circumference effects release of the resulting elastomeric sheath, lifting the same off the positive mold form. An anatomically accurate abbreviated condom having an inwardly projecting wedge between the two bilaterally symmetric lobes of the glans penis is obtained.

19 Claims, 4 Drawing Sheets

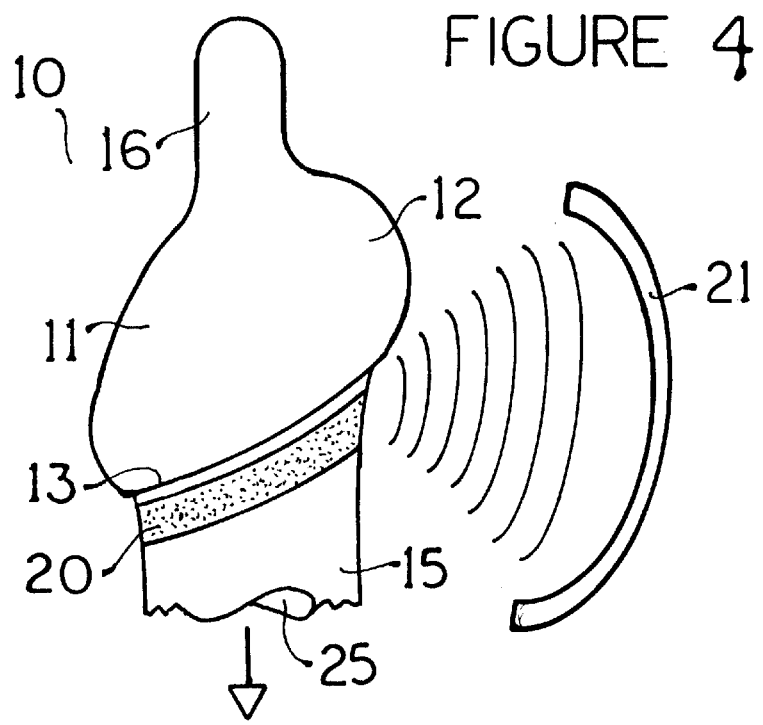
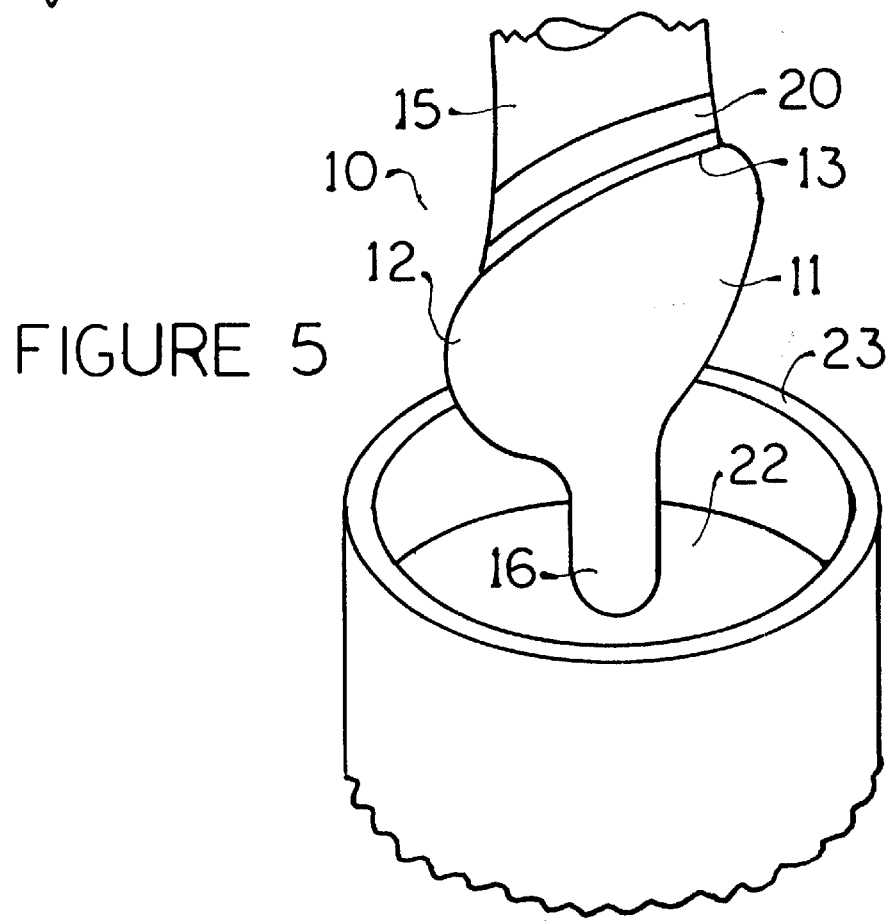

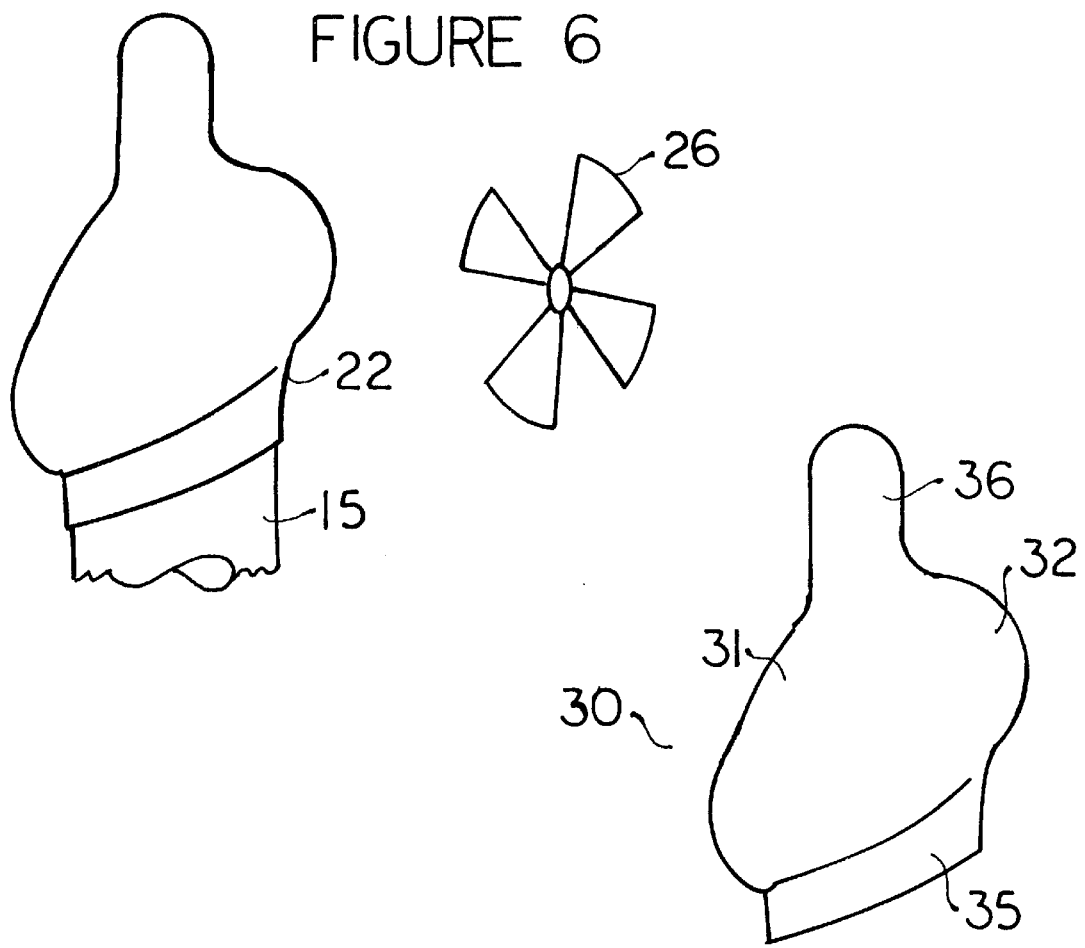
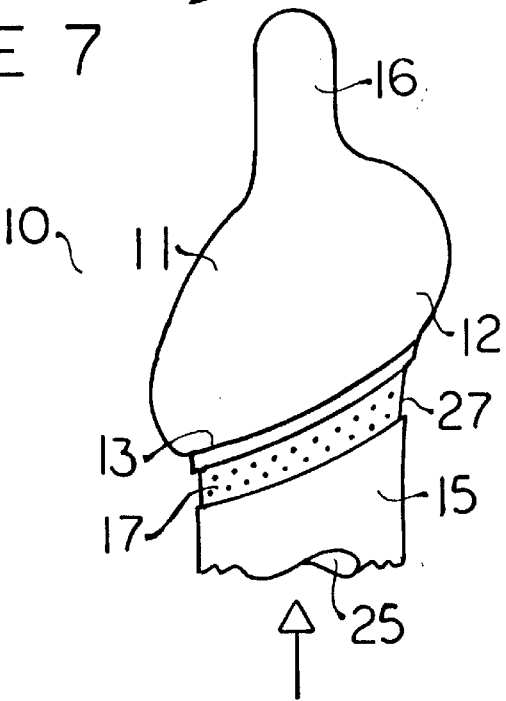

MANUFACTURING METHOD FOR ANATOMICALLY ACCURATE ABBREVIATED CONDOMS

BENEFIT OF EARLIER FILING DATE

This application claims benefit, under 35 U.S.C. 119(e), of the earlier filing date of Provisional Application No. 60/293,223 entitled 'Manufacturing Method For Anatomically Accurate Abbreviated Condoms' filed May $25^{th}$, 2001 in the name of the same inventor and applicant as the present, full, Non-Provisional Application for U.S. Utility Patent: Rory P. Blake of Charlotte, N.C.

BACKGROUND OF THE INVENTION

1. Field of the Invention

The present invention relates generally to condoms, more specifically to abbreviated condoms, and most particularly to methods of manufacturing abbreviated condoms.

2. General Background

Abbreviated condoms are distinguished over conventional condoms by a much shorter, abbreviated, length. Conventional condoms are of sufficient length to encase the entirety of most erect penises including all of the shaft. Abbreviated condoms are of much shorter length intended to enclose just the head of an erect penis while leaving the shaft exposed in order to retain sensitivity and thereby encourage use of the condom. Both types of condom are intended to retain seminal fluid from ejaculation in order to prevent undesired pregnancy and more importantly, as many other types of contraceptives are available, to prevent transmission of sexually transmitted diseases (STDs) between sexual partners for which purpose condoms are the only effective means known.

Abbreviated condoms, in contrast to conventional, full length condoms, differ in two major aspects: (a) means of retaining the condom in position during use; and (b) providing a reservoir for the seminal fluid. Conventional condoms possess sufficient length and volume to utilize an elastic band about the open bottom for sealing the structure against leakage of seminal fluid and provide an inherent reservoir for the seminal fluid resulting from ejaculation. There is no need for a separate reservoir structure in a conventional condom and no need for means other than the elastic band at the open bottom of the condom for securing the condom during use. Abbreviated condoms require, in contrast to conventional full length condoms, a separate distinct reservoir, as well as a particular means of securing the condom in position during use which will prevent inadvertent displacement.

A review of the basic structures employed by abbreviated condoms in addressing these two fundamental problems is given below.

Prior Art

Two different basic forms of reservoirs and two different basic means of retaining an abbreviated condom in position during use are known in various forms in the prior art. An expansible area located in the cleft between the bilateral lobes of the glans penis is one type of reservoir. An expansible structure located directly in front of the opening of the urethra is another basic approach. Either type of reservoir is theoretically independent of the two basic approaches known in the prior art for retention of an abbreviated condom in position during use but an anatomically accurate analysis of the head of an erect penis reveals a correlation between these two aspects and exposes many of the difficulties in the prior art in addressing the problem of retention particularly.

One basic approach to a retention means is similar to that utilized by conventional, full length, condoms: use of an elastic band which, in contrast to the elastic band on a conventional condom, is typically intended to be located behind the glans penis in the sulcus thereby taking advantage of the relative increase in elevation from the shaft to the glans which occurs immediately in front of the sulcus. This approach is disadvantaged, however, by the fact that the elevated ridge immediately in front of the sulcus, which is quite pronounced on the back and top of the head of an erect penis, diminishes to practically nothing at the forward and bottom. This ridge also angles downward and forward which anatomical attribute is often neglected in the structure of many abbreviated condoms of the prior art which erroneously assume radial symmetry.

Use of an elastic band as a retention means for an abbreviated condom is hence hindered by the actual anatomical variance of the glans penis from radial symmetry. If this anatomical variance is observed and the elastic band is left as circular the area underneath the cleft and between the forward lobes of the glans penis may be utilized as a reservoir. This approach is found in U.S. Pat. No. 6,035,854 issued Mar. 14, 2000 to the present inventor, Rory P. Blake, which reference also contains a more detailed review of the prior art with regard to specific references relating to abbreviated condoms. One disadvantage of this approach, however, is the fact that this area beneath and below the bilateral glans is particularly sensitive for which reason it is preferably left exposed.

Another basic approach to retaining an abbreviated condom upon the head of an erect penis which can leave the particularly sensitive area beneath and in between the bilateral lobes of the glans penis is to utilize adhesive. Ideally, the application of an appropriate adhesive about the interior perimeter of an abbreviated condom will retain the same in position during use in a structure which only encloses the head of an erect penis, leaving the particularly sensitive area beneath and in between the bilateral lobes of the glans penis exposed. Nearly all of the prior art, with the notable exception of U.S. Pat. No. 6,035,854 issued Mar. 14, 2000 to the present inventor, assumes radial symmetry in the structure of the head of an erect penis and hence utilizes a radially symmetric abbreviated condom structure which renders the use of adhesive applied to the interior perimeter of an abbreviated condom defective with regard to sealing the same against transmission of bodily fluids including seminal fluid. In brief, unless the true anatomical structure of the head of an erect penis is taken into account the means of retaining an abbreviated condom upon the same is considered less than likely to succeed.

Statement of Need

Location of an expansible reservoir at the tip of an abbreviated condom is problematic for another reason. Several known prior art references utilize an accordion or concertina fold type structure for an expansible reservoir located at the tip. Theoretically this is perhaps ideal but there is no known method of manufacture for such a structure which is considered economically feasible. The assumption of radial symmetry, moreover, which has been demonstrated above to hinder effective means of retention of an abbreviated condom upon the head of an erect penis, is further seen to greatly simplify the method of manufacture. Conventional condoms are typically manufactured by dip molding and machining of the mold for the same is greatly simplified with the assumption of radial symmetry which, owing to the size of these condoms, does not present any problems with regard to retention of the same upon an erect penis. An anatomically accurate abbreviated condom, however, preferably does not assume radial symmetry.

Molding of an anatomically accurate abbreviated condom is considered problematic. With conventional tooling which assumes radial symmetry there is no hindrance to removing the condom from the interior mold structure. An anatomically accurate condom requires an anatomically accurate mold and not only is this unknown in the prior art but if it existed the interior mold structure would resist removal of the condom during manufacture because of the complex curves possessed of the bilaterally symmetric but radially unsymmetric lobes of the glans penis which are considered to characterize any head of any penis erect or flaccid. A need is therefore recognized for an economic manufacturing method for the production of anatomically accurate abbreviated condoms which conform to, and therefore possess, complex curves which are not radially symmetric.

SUMMARY OF THE INVENTION

Objects of the Invention

The encompassing object of the principles relating to the present invention is the provision of an economic method of manufacturing an anatomically accurate abbreviated condom possessing bilaterally symmetric but radially unsymmetric complex curves.

An auxiliary objective of the principles relating to the present invention is the provision of an economic method of manufacturing an anatomically accurate abbreviated condom possessing bilaterally symmetric but radially unsymmetric complex curves utilizing dip molding.

A first ancillary objective of the principles relating to the present invention is the provision of an economic method for the application of adhesive during production of an anatomically accurate abbreviated condom possessing bilaterally symmetric but radially unsymmetric complex curves.

A second ancillary objective of the principles relating to the present invention is the provision of an economic method for the application of an adhesive backing strip during production of an anatomically accurate abbreviated condom possessing bilaterally symmetric but radially unsymmetric complex curves.

A second auxiliary objective of the principles relating to the present invention is the provision of an economic method of manufacturing an anatomically accurate abbreviated condom possessing bilaterally symmetric but radially unsymmetric complex curves having an effective adhesive which is also readily removable.

A third ancillary objective of the principles relating to the present invention is the provision of an economic method of manufacturing an anatomically accurate abbreviated condom possessing bilaterally symmetric but radially unsymmetric complex curves having an effective adhesive which covers only a circumferential band.

Principles Relating to the Present Invention

Regardless of whether injection or dip molding is utilized a rather sophisticated form must be machined which accurately reflects the anatomy of the head of an erect penis. In the case of dip molding one interior positive form mold is concerned which must have an exterior which essentially mimics or reflects, accurately, the actual anatomical shape of the head of an erect penis. In the case of injection molding this positive form is the core and the matching or congruent exterior mold is a slightly larger negative of the same form. The form itself in any case is, as mentioned earlier, fully sculptured and includes complex curves which impede release from the interior positive form required of molding an anatomically accurate abbreviated condom in any manner.

This type of form requires machining with use of a computer guided milling machine using appropriately shaped milling heads which requires a computer program to direct the motion of the tool head during machining generated from a three dimensional computer graphic model. The generation of this model is essentially art and is not considered feasible unless the anatomy of the glans penis is fully appreciated by the artist generating this model. It is not possible, in other words, if the bilaterally lobed fully sculptured complex curved form of the head of an erect penis is simplified as being radially symmetric.

In achievement of the objectives given above it is first considered that the complex curves involved impose an undercut to the positive form which impedes release of the product in manufacture and that use of synthetic, polymeric, materials as opposed to natural latex exacerbates this impediment but is preferred for several reasons. Effective prevention of the transmission of STDs including HIV during sexual activity is the primary reason. Natural latex generally does not provide as effective a barrier against transmission as polymeric materials. A second reason is that significant, widespread, allergies to natural latex have developed in the human population in the last twenty-five years which phenomenon is largely credited, along with the increased incidence of STDs including HIV, with the replacement of latex by polymeric material having elastic qualities, i.e. elastomers, for the manufacture of condoms in recent years.

It is suggested that the impediment posed by the undercut of the complexly curved surfaces necessary be addressed with a positive mold form which possesses a bore and at least one aperture in communication therewith through which positive pressure can be introduced. This expands the product and lifts the same off the positive mold form. It is further considered that a circumferential adhesive layer is desired to ensure the prevention of fluid transmission and that a backing strip for the adhesive is desirable.

This backing strip necessarily has some rigidity and must be held flush against the positive mold form in order to ensure interior disposition. A perforated circumference of location and dimensions appropriate for the dimensions of the backing strip disposed about the positive mold form is suggested through which negative pressure can be applied. A shallow relief in the exterior surface of the positive mold of the thickness of the backing strip is also recommended for the purpose of ensuring interior disposition of the backing strip.

Negative pressure applied through the bore of the positive mold form to this perforated circumference retains the backing strip in correct disposition during application of an adhesive layer upon the exterior surface of the same, curing of the adhesive layer, coating the positive mold form with liquid polymeric material having elastic qualities, i.e. liquid elastomer, and curing of the liquid elastomer into the solid sheath product at which time the pressure is reversed and the finished product is lifted off the positive mold form.

It is further desired that the adhesive utilized be readily removed from the penis after use without causing pain and this essentially requires an adhesive which loses its adhesive qualities under readily obtained circumstances. It is suggested that a water soluble adhesive be utilized for this purpose which is sensitive to isotonic solution and hence maintains adhesion in contact with all bodily fluids. Tap water can be used to dissolve the adhesive layer for easy and comfortable removal of the condom after use while the tonicity of bodily fluids assures adhesion during use. Sulfopolyester adhesive is particularly recommended which is cured with ultraviolet (UV) radiation.

It is also particularly suggested that the positive mold form be coated with liquid elastomeric in a bath and that adhesive be applied in a directed dispersion, i.e. with a spraying operation, with the backing strip held by negative pressure through the perforated circumference. It is suggested that a simple reservoir be located directly in front of the urethra opening and that the perforated circumference, which locates the backing strip and adhesive, be located immediately behind the corona of the glans penis upon the margin adjacent the open end of the abbreviated sheath.

BRIEF DESCRIPTION OF THE DRAWINGS

FIG. 4 is a plain elevational side view of a positive mold form with a backing strip thereupon coated with a layer of adhesive being cured by ultraviolet radiation in depiction of step D of FIG. 1.

FIG. 5 is a plain elevational side view of a positive mold form with a backing strip thereupon coated with a cured layer of adhesive receiving a liquid elastomer coating in depiction of step E of FIG. 1.

FIG. 6 is a plain elevational side view of a positive mold form with a liquid elastomer coating thereupon being air cured in depiction of step F of FIG. 1.

FIG. 7 is a plain elevational side view of a positive mold form and an abbreviated condom made in preferred accordance with the principles relating to the present invention being released by positive pressure in depiction of step F of FIG. 1.

Figure 1:
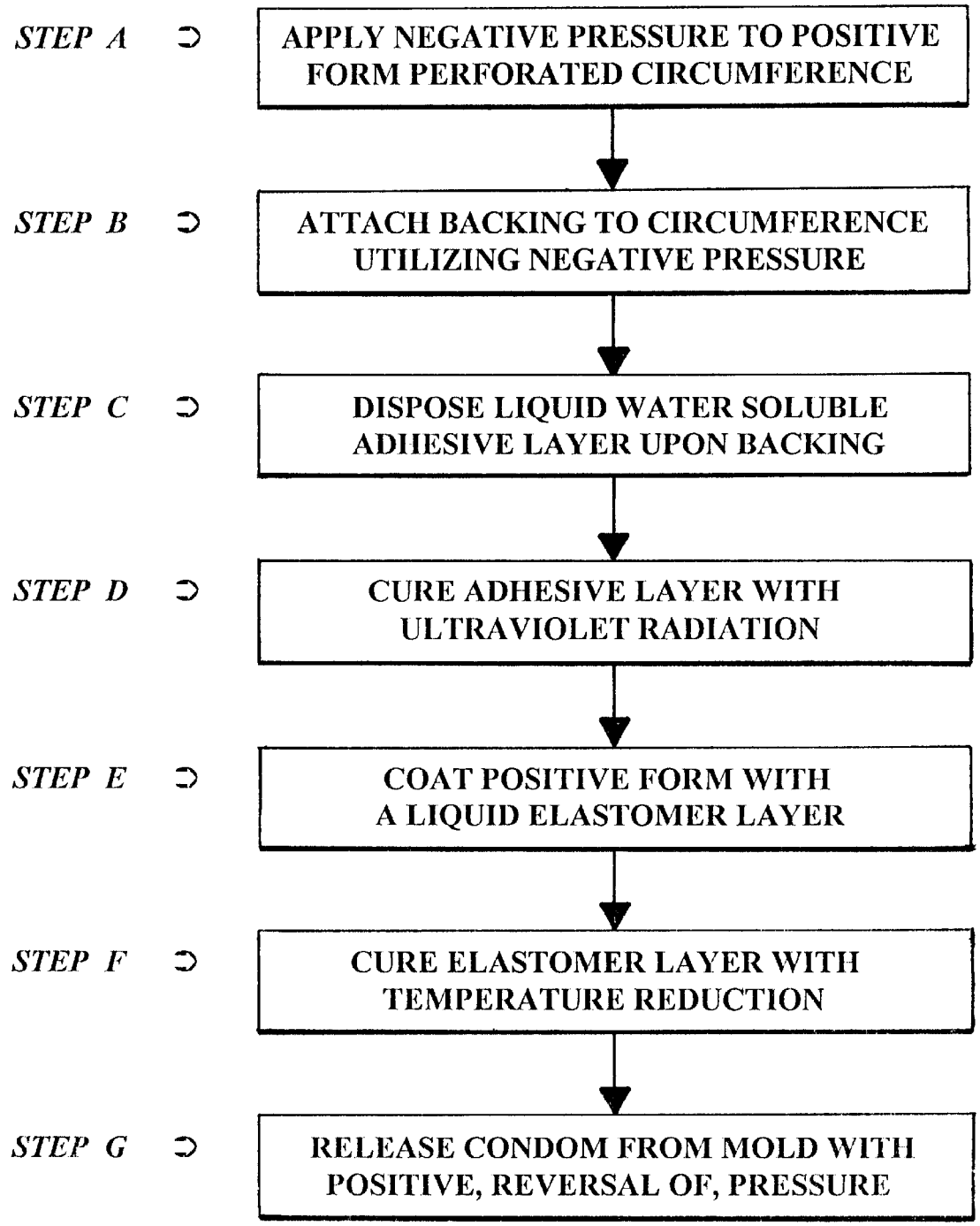
FIG. 1 is a schematic depiction of basic steps A–G followed in preferred accordance with the principles relating to the present invention.

| NOMENCLATURE | |
|---|---|
| 10 | positive mold form |
| 11 | head portion |
| 12 | lobe portion |
| 13 | ridge line |
| 15 | shaft portion |
| 16 | reservoir portion |
| 17 | perforated circumference |
| 19 | backing strip |
| 20 | adhesive |
| 21 | UV radiation source |
| 22 | liquid elastomer |
| 23 | open container |
| 25 | bore |
| 26 | electric fan |
| 27 | circumferential relief |
| 29 | free end |
| 30 | abbreviated condom |
| 31 | head |
| 32 | lobe |
| 33 | corona |
| 35 | marginal shaft |
| 36 | reservoir |
| 37 | wedge |

DETAILED DESCRIPTION OF THE PREFERRED EMBODIMENT

The first concern with regard to economic manufacture of an abbreviated condom is the type of manufacture. It is considered that molding, broadly, is the only practical approach since the product must be water proof, flexible, and preferably elastic. An 'elastomer' is noted to be defined by the American Society for Testing and Materials as "a polymeric material which at room temperature can be stretched to at least twice its original length and upon immediate release of the stress will return quickly to approximately its original length." The term 'elastomer' is understood herein to reflect the essential characteristic of elasticity conveyed by this definition while recognizing that a polymeric material which can be stretched to 175% of its length at rest without damage has essentially half the elasticity of a material which can be stretched to 250% It is recognized that "certain of the polyethylenes" "approach this (ASTM definition) rubberlike state"(*Materials Handbook*, 13$^{th}$ *Edition*, McGraw-Hill, Inc., 1991, page 284). It is also noted that "a number of plastics have elastomer grades, such as the olefins, styrenes, fluoroplastics, and silicones." (Ibid.)

It is also considered that the full flexibility possessed of a conventional full length condom is, not necessary if different sizes are manufactured. Also, while the plasticized polypropylene commonly utilized for conventional condoms currently is considered satisfactory it is recommended that the typical thickness of approximately 0.0024" be increased in order to provide better protection against transmission of the human immunodeficiency virus (HIV) which, though typically transmitted in whole cells, can be transmitted by itself A doubling of the typical conventional thickness is hence suggested and if the same material is utilized a commensurate decrease in flexibility is anticipated. Retention by adhesive is hence recommended though the use of multiple sizes is preferably avoided In comparison with a conventional full length condom an abbreviated condom 30 manufactured in preferred accordance with the principles relating to the present invention, as seen in FIG. 7, with twice the wall thickness and effective use of adhesive, is considered to provide better protection against the propagation of HIV and other STDs.

The essential concern for production of an anatomically accurate abbreviated condom 30 is the release of the product from the positive mold form 10 owing to the possession of an interior cavity containing complex curves imposing undercuts necessary to accurate reflect anatomically the head of the penis which is considered to be characterized by the possession of bilaterally symmetric but radially unsymmetric lobes of the glans penis. An anatomically accurate abbreviated condom 30 is not easily released from a positive mold form because of the complex contours involved. The first area of concern is the cleft between the two lobes of the glans penis. If the abbreviated condom 30 encloses the ridge or corona which is pronounced upon the upper rear portion of the head of a penis and is intended to conform to the sulcus behind the corona as well then this area is also of concern as a hindrance to release of the product from the positive mold form 10.

An exterior mold structure required of injection molding is not problematic because it is readily and typically comprised of two separable parts. In order to release product comprising an anatomically accurate abbreviated condom 30 from a positive mold form 10 it is suggested that the latter possess a bore 25 communicating with at least one exterior orifice located in or preferably directly below, areas having inward inflection of the complex curves possessed of said positive mold form 10. A pressurized fluid, preferably air, is then forced through said bore 25 to each said orifice after the liquid comprising the material from which the product is made has hardened.

Figure 2:
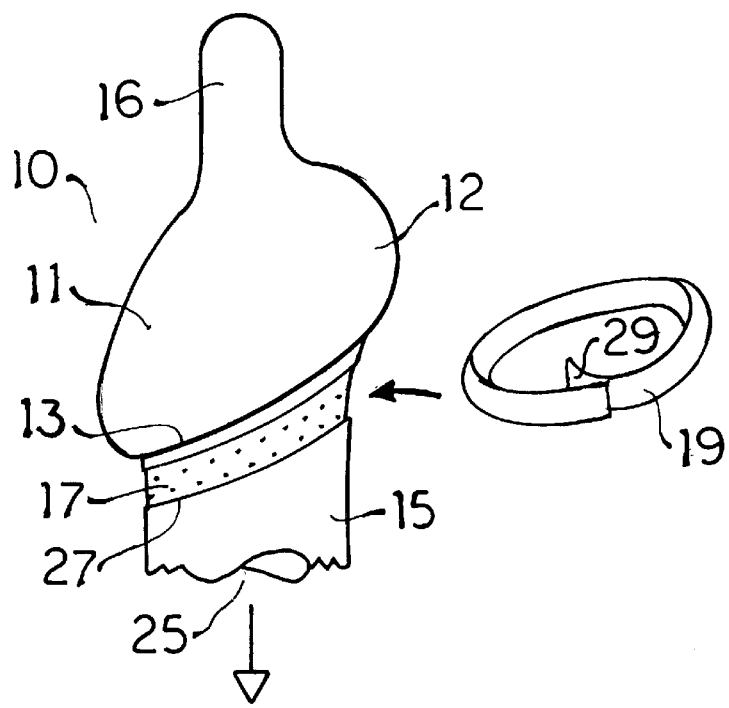
FIG. 2 is a plain elevational side view of a positive mold form having negative pressure applied and a backing strip to be applied in depiction of steps A & B of FIG. 1.

Manufacture in preferred accordance with the principles relating to the present invention is illustrated in FIGS. 2–7 and is summarized by STEPS A–G as depicted in FIG. 1. As clearly seen in FIG. 2 it is preferred that a perforated circumference 17 be utilized for both introduction of positive air pressure for release, as illustrated in FIG. 7, and application of negative pressure to hold a backing strip 19 for an adhesive 20 layer. This perforated circumference 17 is further preferably located, as seen in FIG. 2, upon an upper exterior area of the shaft portion 15 of the positive mold form 10 below or behind the ridge line 13 defining the bottom or back of the head portion 11 including two bilaterally symmetric but radially unsymmetric lobe portions 12. This determines location of the backing strip 19 and the adhesive 20 layer applied thereupon.

Figure 3:
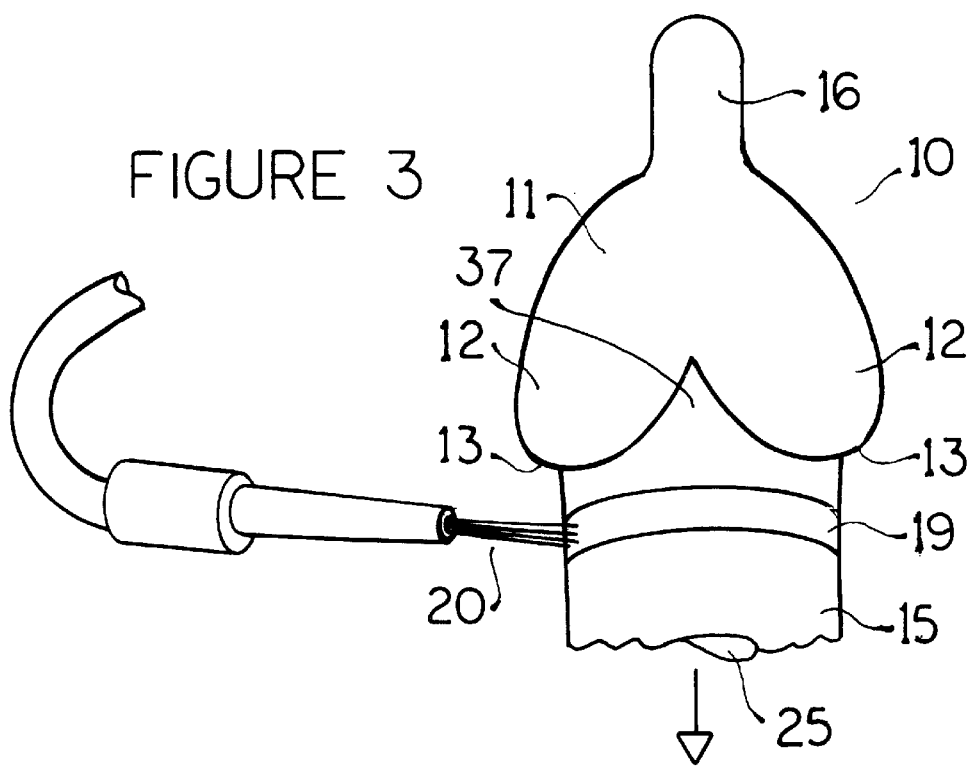
FIG. 3 is a plain elevational front view of a positive mold form with a backing strip thereupon having adhesive applied in depiction of step C of FIG. 1.

It is preferred that the adhesive 20 be applied to the exterior surface of the backing strip 19 in a directed dispersion as depicted in FIG. 3 while negative pressure continues to hold the backing strip 19 in place. Application in this manner is preferred because a spraying operation of this kind is readily automated. This is hence opposed to brushing the adhesive 20 on which is more suited to manual operation. It is also suggested that the perforated circumference 17 also include a shallow circumferential relief 27 of a depth approximately equivalent to the thickness of the backing strip 19 thereby ensuring that the same is interior to the elastomeric sheath. More importantly perhaps it is preferred, as indicated in STEP C in FIG. 1, that the adhesive 20 utilized be water soluble to permit comfortable removal after use.

Otherwise it is suggested that another location excluding the area immediately behind the cleft between the two lobe portions 12 be utilized for a perforated circumference 17, the backing strip 19, and hence the adhesive 20 as this area is particularly sensitive and only a water soluble adhesive 20 is known to provide a satisfactory means of removal in this case. It is further emphasized that the adhesive 20 preferably, if water soluble, also be sensitive to tonicity and maintain full adhesion when immersed in isotonic fluid. A sulfopolyester adhesive 20 is specifically suggested. Eastman Chemical Company's AQ product is known to possess satisfactory characteristics. Adhesion is unaffected by any body fluid but the adhesive 20 is soluble in tap water.

As indicated in STEP D of FIG. 1 a preferred water soluble adhesive 20 can be cured with ultraviolet (UV) radiation. This step is further depicted in FIG. 4 wherein an exteriorly located UV radiation source 21 is seen which effectively surrounds the positive mold form 10 and the liquid adhesive 20 layer on the backing strip 19 held by negative pressure applied through the perforated circumference 17. This arrangement permits use of any material for the positive mold form 12 10 but it is actually preferred that the UV radiation source 21 comprise a single bulb located within the bore 25 of a positive mold form 10 made of glass or other suitably transparent material. Glass also presents a very smooth, hard, surface which facilitates removal of the product form from the positive mold form 10. It is also suggested that a transparent backing strip 19 be used in this case.

It is further considered that this step of curing a preferred water soluble adhesive 20 layer can be deferred until after coating of the upper part of the positive mold if an internal UV radiation source 21 is utilized or if a substantially transparent liquid elastomer 22 is utilized. If the backing strip 19 is also substantially transparent then this step of curing a preferred water soluble adhesive 20 layer can be deferred until after release of the cured elastomer sheath product with use of an external UV radiation source 21. If an internal UV radiation source 21 is utilized after release of the product from the positive mold form 10 only the backing strip 19 must be substantially transparent. It is further considered desirable to have two stages of curing a preferred liquid adhesive 20 with a UV radiation source 21: the first prior to coating with liquid elastomer 22 and a second afterward, preferably after release of the product, in order to promote quicker mold cycling time. It is also considered that curing of the liquid adhesive 20 with a UV radiation source 21 may also be necessary if another type other than the type requiring this is found to be satisfactory: i.e. water soluble but effective in isotonic immersion.

STEP E of FIG. 1 indicates coating of the positive mold form 10 with liquid elastomer 22, which, as depicted in FIG. 5, is preferably accomplished by dipping the positive mold form 10 into a bath of liquid elastomer 22 held in an open container 23 preferably heated to maintain the elastomer in a liquid form. It is also preferred that the liquid elastomer 22 possess a low melting point: i.e. below boiling. The liquid elastomer 22 can, alternatively, be applied in a directed dispersion similar to the recommended means of applying the liquid adhesive 20 layer. Or the positive form mold 10 can be coated by liquid elastomer 22 in an injection molding. In any case the liquid elastomer 22 coating encompasses the backing strip 19 held by negative pressure applied through the perforated circumference 17 and all of the head portion 11 and reservoir portion 16 above this. The liquid elastomer 22 can be natural latex, not a polymeric material, if dip molded but, because latex is comparatively porous compared to plastics including polyethylene and polypropylene in preventing transmission of STDs and owing to the development of allergy to latex by humans in recent years, polyethylene or other suitable polymeric liquid elastomer 22 is preferred.

In the case of injection molding this material is necessarily plastic. In the case of dip molding the hardening, i.e. curing, of the liquid elastomer 22 is preferably effected by direct gaseous convection effecting temperature reduction, i.e. air cooling, or by liquid conduction or convection, i.e. in still or moving contact with a liquid bath, preferably cold water. A water dispersion is also considered satisfactory. In the case of injection molding this hardening is preferably effected by indirect liquid convection, i.e. water cooling.

In any case curing of the liquid elastomer 22 layer upon the positive mold form 10 is effected by temperature reduction, as indicated by STEP F in FIG. 1, which aspect characterizes thermoplastics. The electric fan 26 depicted in FIG. 6 is therefore understood as representative of any means of cooling the liquid elastomer 22 layer thereby effecting curing of the same into a solid elastomer 22 sheath of the desired configuration and dimensions. In the case of injection molding cooling is normally effected with cold water run through the exterior mold. In the case of dip or spray molding liquid elastomer 22 onto a positive mold form used alone as depicted in FIGS. 2–7 either convective air or cold water bath cooling is recommended.

It is noted that in STEPS A–F as depicted in FIGS. 2–6 a negative pressure has been preferably exerted, and maintained, upon a perforated circumference 17 through the bore 25 of the shaft portion 15 of the positive mold form 10. This is readily achieved with a simple hose connection to a vacuum source, e.g. a reversed compressor, in the case of a dip, spray, or injection molding operation. It is recognized, moreover, that all of the other aspects required of preferred accordance with the principles relating to the present invention are applicable to molding by any means using a positive mold form 10 but that the use of a backing strip 19 held by negative pressure to which an adhesive 20 layer is applied prior to coating of the positive mold form 10 with liquid elastomer 22 comprise steps which are readily automated but are necessarily external to an injection molding and that dip or spay molding is preferred over injection molding for this reason. And it is further noted that maintenance of this negative pressure upon a perforated circumference 17 is not strictly necessary after curing of the liquid adhesive 20 layer if this step results in a sufficiently strong cincture In any case the application of positive pressure through the bore 25 of the shaft portion 15 to external orifices located in the perforated circumference 17 after curing of the elastomer 22, which is preferably a reversal of the negative pressure previously maintained, obtains efficient release of the product from the positive mold form 10 as depicted in FIG. 7 and indicated by STEP G of FIG. 1. The resulting product, an anatomically accurate abbreviated condom 30 manufactured in preferred accordance with the principles relating to the present invention, is lifted off the positive mold form 10 by the positive pressure introduced through the perforated circumference 17 and has a head 31 including a frontally disposed reservoir 36, two bilaterally symmetric but radially unsymmetric lobes 32 separated by an inwardly projecting wedge 37, and a circumferential corona 33 separating the head from a marginal shaft 35.

The interior surface of the abbreviated condom 30 possesses the same configuration as the exterior surface of upper part of the positive mold form 10 including the head portion 11, bilateral lobe portions 12, ridge line 13, and a margin of the shaft portion 15 with an adhesive 20 layer circumscribing the same and covered by the backing strip 19 with an interiorly exposed 'pull tab', i.e. an interiorly overlapping free end 29 of the backing strip 19 seen in FIG. 2, readily grasped for removing the backing strip 19 to expose the adhesive 20 and position the abbreviated condom 30 for use. With regard to the reservoir 36 it is recommended that a simple, blunt, projection forward of the tip of the abbreviated condom 30 be utilized as seen in FIG. 7. Location directly in front of the urethra opening is desirable as is a volume sufficient to fully accommodate any single ejaculation of seminal fluid. This location at the forward closed end of the condom facilitates both collection of an ejaculation during use and ease in manufacture by molding using a positive mold form 10.

As a last step in a practical manufacturing method of anatomically accurate abbreviated condoms 30 packaging is recommended as is the maintenance of clean if not substantially sterile conditions throughout but particularly with regard to handling of the cooled product after release from the mold utilized through the process of packaging the product. The packaging is preferably of a conventional foil or plastic variety.

It is also particularly suggested that the positive mold form be coated with liquid elastomeric in a bath and that adhesive be applied in a directed dispersion, i.e. with a spraying operation, with the backing strip held by negative pressure through the perforated circumference. It is suggested that a simple reservoir be located directly in front of the urethra opening and that the perforated circumference, which locates the backing strip and adhesive, be located immediately behind the corona of the glans penis upon the margin adjacent the open end of the abbreviated sheath.

The foregoing is intended to provide the best known manner of exercising the principles relating to the present invention in preferred accordance with the same and is not to be interpreted in any manner as restrictive of the scope of said invention or the rights and privileges obtained by Letters Patent in protection thereof and for which I claim:

1. A method for the manufacture of abbreviated condoms intended to possess interior anatomical accuracy comprising the steps of:

applying negative pressure internally through a bore of a shaft portion to a perforated circumference of a positive mold form and possessing a reservoir portion and a head portion including two bilaterally symmetric lobe portions;

attaching a backing strip to said perforated circumference utilizing said negative pressure to hold said backing strip in position;

disposing a layer of liquid adhesive upon the exterior surface of said backing strip held in position by said negative pressure applied to said perforated circumference;

coating an upper part of said positive mold form including said reservoir portion and said head portion with a liquid elastomer layer;

curing said elastomer layer coating upon said upper part of said positive mold form with temperature modification;

applying positive pressure to said perforated circumference through said bore of said shaft portion of said positive mold form; thereby releasing said cured elastomer layer in the form of a sheath possessing a reservoir, a head including two bilaterally symmetric lobes separated by an inwardly projecting wedge having adhesive interiorly attached thereto and interiorly covered by said backing strip.

2. The method of claim 1 wherein said perforated circumference is located in a shallow relief possessing a depth approximately equal to the thickness of the backing strip.

3. The method of claim 1 wherein the step of attaching a backing strip to said perforated circumference leaves an interiorly overlapping free end of said backing strip.

4. The method of claim 1 wherein the step of disposing a layer of liquid adhesive upon the exterior surface of said backing strip is accomplished using a directed dispersal.

5. The method of claim 4 wherein the step of disposing a layer of liquid adhesive upon the exterior surface of said backing strip is accomplished using a directed dispersal in an automated spraying operation.

6. The method of claim 1 wherein the step of coating an upper part of said positive mold form with a liquid elastomer layer is accomplished using a directed dispersal.

7. The method of claim 1 wherein the step of coating an upper part of said positive mold form with a liquid elastomer layer is accomplished using a bath of liquid elastomer in an open container.

8. The method of claim 7 wherein the step of coating an upper part of said positive mold form with a liquid elastomer layer is accomplished using a heated bath of liquid elastomer in an open container.

9. The method of claim 1 wherein the step of curing said elastomer layer coating upon said upper part of said positive mold form with temperature modification is accomplished with a cold water bath.

10. The method of claim 1 wherein the step of curing said elastomer layer coating upon said upper part of said positive mold form with temperature modification is accomplished with forced air convection.

11. The method of claim 10 wherein the forced air convection is provided by at least one electric fan.

12. The method of claim 1 further including the step of curing said liquid adhesive layer using an ultraviolet (UV) radiation source.

13. The method of claim 12 wherein said UV radiation source is external to said positive mold form.

14. The method of claim 12 wherein said UV radiation source is internal to said positive mold form which is further made of a substantially transparent material.

15. The method of claim 14 wherein said backing strip is further made of a substantially transparent material.

16. The method of claim 12 wherein said step of curing said liquid adhesive layer using said UV radiation source is performed prior to said step of coating an upper part of said positive mold form with a liquid elastomer layer.

17. The method of claim 12 wherein said step of curing said liquid adhesive layer using said UV radiation source is performed after said step of coating an upper part of said positive mold form with a liquid elastomer layer.

18. The method of claim 17 wherein said liquid elastomer layer is substantially transparent.

19. The method of claim 18 wherein the step of curing of said liquid adhesive layer using said UV radiation source is performed after the step of releasing said cured elastomer layer in the form of a sheath.

* * * * *